US005977187A

United States Patent [19]
Frydman et al.

[11] Patent Number: 5,977,187
[45] Date of Patent: Nov. 2, 1999

[54] 4-SUBSTITUTED-1,2-NAPHTHOQUINONES AND THEIR USE IN THE INHIBITION OF NEOPLASTIC CELL GROWTH

[75] Inventors: Benjamin J. Frydman; Donald T. Witiak; Laurence J. Marton; Karen Neder, all of Madison, Wis.; M. Eileen Dolan, Oak Park, Ill.

[73] Assignee: Wisconsin Alumni Research Foundation, Madison, Wis.

[21] Appl. No.: 09/172,044

[22] Filed: Oct. 14, 1998

Related U.S. Application Data

[60] Division of application No. 08/744,631, Nov. 6, 1996, Pat. No. 5,883,270, which is a continuation-in-part of application No. 08/604,131, Feb. 20, 1996, Pat. No. 5,824,700.

[51] Int. Cl.$^6$ .................. A61K 31/135; A61K 31/10; A61K 31/075; A61K 31/05
[52] U.S. Cl. .................. 514/717; 514/657; 514/712; 514/715; 514/732
[58] Field of Search .................. 514/657, 712, 514/715, 717, 732

[56] References Cited

U.S. PATENT DOCUMENTS

| | | |
|---|---|---|
| 4,879,243 | 11/1989 | Mura et al. . |
| 4,882,339 | 11/1989 | Wasley . |
| 5,053,053 | 10/1991 | De Labbey et al. . |

FOREIGN PATENT DOCUMENTS

| | | |
|---|---|---|
| 3926747 A1 | 2/1991 | Germany . |
| WO 94 03163 | 2/1994 | WIPO . |
| WO 94 11382 | 5/1994 | WIPO . |
| WO 95 12588 | 5/1995 | WIPO . |
| WO 96 33988 | 10/1996 | WIPO . |

OTHER PUBLICATIONS

Bullock et al., Antiprotzoal Quinones. II. Synthesis of 4–amino–1,2–naphthoquinones and related compounds as potential antimalarials, *J. Med. Chem.* (1970), vol. 13(1), pp. 97–103.

Cassis et al., Studies on Quinones. VIII(I): The application of Michael adducts from 2–hydroxy–1,4–naphthoquinones for the preparation of dihydronaphthopyrandiones, *Journal of Heterocyclic Chemistry* (Mar. 1982), vol. 19, No. 2, pp. 381–384.

Driscoll et al., Structure–Antitumor Activity Relationships Among Quinone Derivatives, *Cancer Chemotherapy Reports,* (1974) Part 2, vol. 4, No. 2, pp. 1–27 and 331–351.

Dunn, Structure–activity analyzed by pattern recognition: The asymmetric case, *J. Med. Chem.,* (1980), vol. 23(6), pp. 595–599.

Fieser, Louis, F., The Alkylation of Hydroxynaphthoquinone. I. Ortho–Ethers, *J. Am. Chem. Soc.,* (1926), vol. 48, pp. 2922–2937.

Fieser, Louis F., The Alkylation of Hydroxynaphthoquinone. III. A Synthesis of Lapachol, *J. Am. Chem. Soc.,* (1927), vol. 49, pp. 857–864.

Fieser, Louis F., The Reduction Potentials of Various Naphthoquinones, *J. Am. Chem. Soc.,* (1935), vol. 57, pp. 491–494.

Gupta et al., Bromination with N–brumosuccinimide, Part III. Formation of 3'–bromo–beta–lapachone, dehydroiso–beta–lapachone and 4'–bromo–iso–beta–lapachone from lapachol, *Chemical Abstracts* (Sep. 15, 1980, Columbus, OH), vol. 93, No. 11, p. 705.

Gupta et al., Direct oxidation of 1–naphthaldehydes to 2–substituted 1,4–naphthoquinones: application to the chemoselective syntheses of Stuttgart, DE), No. 6, pp. 355–357.

Kakisawa et al., Synthesis of Furonaphthoquinones, *Bulletin of The Chemical Society of Japan* (Mar. 1970, Tokyo, JP), vol. 43, No. 3, pp. 824–826.

Kobayashi et al., Photoinduced molecular transformations. Part 127. A new [2+2] photoaddition of 2–amino–1,4–naphthoquinone with vinylarenes . . . , *Journal of Chemical Society, Perkin Transactions I.* (Jan. 1992), No. 1, pp. 115–121.

Krohn et al., Synthesis of 6–deoxycryptosporin and related compounds, *Chem. Ber.* (1978), vol. 111(4), pp. 1284–1293.

Lopes et al., In vitro and in vivo evaluation of the toxicity of 1,4–napthoquinone and 1,2–naphthoquinone derivatives against trypanosoma Cruzi, *Annals of Tropical Medicine and Parasitology* (Dec. 1978, London, GB), vol. 72, No. 6, pp. 523–531.

Mackenzie et al., Quinones. Part 11. The Reaction of o–Aminothiophenol with o–Benzo– and o–Naphtho–quinones: A New Route to 1H–Phenothiazin–1–ones, *J. Chem. Soc. Perkin Tran. I,* (1986), pp. 2233–2241.

Takuwa et al., Addition of alcohol to 1,2–naphthoquinone promoted by metal ions. Facile synthesis of 4–alkoxy–1, 2–naphthoquinones, *Bull. Chem. Soc. Jpn.,* (1986), 59(9), 2959–61.

Schaffner–Sabba et al., Beta–Lapachones: synthesis of derivatives and activities in tumor models, *Journal of Medicinal Chemistry* (Aug. 1984, Washington, D.C., USA), vol. 27, No. 8, pp. 990–994.

Bullock et al., J. Med. Chem., vol. 13(1), pp. 97–103, 1970.

*Primary Examiner*—José G. Dees
*Assistant Examiner*—Barbara Badio
*Attorney, Agent, or Firm*—DeWitt Ross & Stevens S.C.

[57] ABSTRACT

Novel 4-substituted-1,2-naphthoquinones, pharmaceutical unit dosage forms containing 4-substituted-1,2-naphthoquinones, and uses of 4-substituted-1,2-naphthoquinones to inhibit the growth of cancer cells are disclosed.

10 Claims, 14 Drawing Sheets

4-SUBSTITUTED-1,2-NAPHTHOQUINONES AND THEIR USE IN THE INHIBITION OF NEOPLASTIC CELL GROWTH this is a divisional of application Ser. No. 08/744,631 filed Nov. 6, 1996, now U.S. Pat. No. 5,883,270, which is a CIP of co-pending application Ser. No. 08/604,131 filed Feb. 20, 1996, now U.S. Pat. No. 5,824,700.

FIELD OF THE INVENTION

The present invention is directed to novel 4-substituted-1,2-naphthoquinones and the use of 4-substituted-1,2-naphthoquinones in the inhibition of neoplastic cell growth.

DESCRIPTION OF THE PRIOR ART 1,2-naphthoquinones (also known as ortho-naphthoquinones, and referred to hereinbelow as o-naphthoquinones) have been widely investigated and find use in several different technological fields. For instance, German Patent Publication (Offenlegungsschrift) DE 3 926 747 A1 describes a large number of o-naphthoquinones having various substituents at the 4-position. These compounds are described as having fungicidal activity.

A 1974 report from the National Cancer Institute (Driscoll et al.) contains structure-activity data for more than 1,500 quinone derivatives using several different in vivo mice models. The cancer types utilized in the in vivo mice models include L1210 (a leukemia), and W-256, CA-755, and S-180 (solid tumors). KB cancer cells were utilized for in vitro cytotoxicity testing. This reference contains a description of 4-ethoxy-1,2-napthoquinone (entry 1484) and its lack of in vitro cytotoxicity against KB cancer cells. The reported $ED_{50}$ is 8.0 µg/mL. As stated in the report itself, a compound is not considered cytotoxic unless it displays an $ED_{50} \leq 4.0$ in the in vitro KB cell model.

Mura et al., U.S. Pat. No. 4,879,243, describe the use of 4-methoxy-1,2-naphthoquinone and 4-methoxycarbonyhmethoxy-1,2-naphthoquinone as electron transfer agents in an assay for the detection of cells in urine.

U.S. Pat. No. 4,882,339, to Wasley, describes several 4-amino-substituted-1,2-dihydroxynaphthalene compounds which are reported to have inhibitory activity against 5-lipoxygenase. The 1,2-dihydroxynaphthalenes are synthesized via reduction of a corresponding 4-amino-1,2-naphthoquinone.

SUMMARY OF THE INVENTION

The invention is drawn to a method of inhibiting growth of cancer cells, including the growth of multiple-drug resistant cancer cells, adriamycin-resistant cancer cells, teniposide-resistant cancer cells, and vinblastine-resistant cancer cells. The method comprises treating the cancer cells with an effective growth-inhibiting amount of a compound of Formula I:

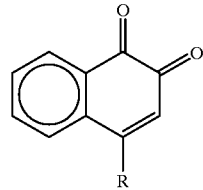

wherein R is selected from the group consisting of $C_3$–$C_8$ linear or branched alkyloxy, $C_3$–$C_8$ linear or branched alkenyloxy, $C_3$–$C_8$ linear or branched amino, $C_3$–$C_8$ alkylthio, and $C_1$–$C_8$ linear or branched substituted alkyloxy, alkenyloxy, amino, and alkylthio, substituted with one or more substituents selected from the group consisting of cycloalkyl, cycloalkenyl, cycloaryl, benzyl, and amino; pharmaceutically-suitable salts thereof, and combinations thereof.

It is preferred that the method be administered to a human cancer patient in need thereof.

The invention is further drawn to pharmaceutical unit dosage forms to practice the above-described method. The pharmaceutical unit dosage forms comprise an amount of a compound of Formula I:

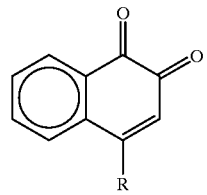

wherein R is selected from the group consisting of $C_5$–$C_8$ linear, branched, or cyclic alkyloxy, $C_5$–$C_8$ linear or branched alkenyloxy, $C_5$–$C_8$ linear or branched amino, $C_3$–$C_8$ alkylthio, and $C_4$–$C_8$ linear or branched substituted alkyloxy, alkenyloxy, amino, and aildytlio substituted with one or more substituents selected from the group consisting of cycloalkyl, cycloalkenyl, cycloaryl, benzyl, and amino; pharmaceutically-suitable salts thereof, and combinations thereof; wherein the amount is effective to inhibit growth of cancer cells in a human cancer patient following administration thereto.

The invention is further drawn to compounds of Formula I:

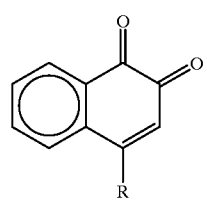

wherein R is selected from the group consisting of $C_5$–$C_8$ alkyloxy, cyclohexyl-$C_5$–$C_8$-alkyloxy, $C_5$–$C_8$ alkenyloxy, and $C_3$–$C_8$ linear or branched alkylthio. Specifically drawn from within this group, the present invention is drawn to 4-(n-pentylthio)-1,2-naphthoqusnone, 4-(3-methyl-butyloxy)-1,2-napthoquinone, 4-cyclohexylmethyloxy-1,2- naphthoqusnone, 4-(2-pentenyloxy)-1,2-naphthoqusnone, and 4-(n-heptyloxy)-1,2-naphthoqusnone napthoquinone. These compounds find use as powerful inhibitors of neoplastic cell growth.

The biological activity of the compounds described herein is remarkable in that the compounds are potent inhibitors of neoplastic cell growth and proliferation at extremely low concentrations. Even more remarkable, the compounds of Formula I display activity against adriamycin-resistant (ADR-resistant) neoplastic cell lines, as well as multi-drug resistant (MDR) neoplastic cell lines. The compounds described herein find use as chemotherapeutic agents in the treatment of a wide range of neoplasms, including cancers of the prostate, breast, colon, brain, and lung. The compounds exhibit their anti-proliferative effects in heretofore unknown, minute concentrations.

In light of the powerful biological activity of these compounds in inhibiting cancer cell growth and proliferation, another aspect of the present invention is drawn to a method of inhibiting growth of cancer cells by treating cancer cells, either in vivo or in vitro, with one or more compounds described herein.

The present method for the inhibition of neoplastic cell growth has both in vivo and in vitro applications. In vivo, the method encompasses the therapeutic treatment of neoplastic growths in mammals, including humans. The treatment includes administering an effective cancer cell growth-inhibiting amount of a compound as described above to a person or animal in need thereof. In vitro, the method for neoplastic cell growth inhibition is effective for inhibiting the proliferation of a large number of different human cancer cell lines, including breast cancer, lung cancer, colon cancer, brain cancer, and prostate cancer. As such, the compounds are useful in the study of the development of resistance to a given structural class of chemotherapeutics.

In light of the above discussion, a principal aim of the present invention is to provide novel compounds and pharmaceutical compositions which inhibit the growth of cancer cells both in vitro and in vivo at very low dosages.

Another aim of the present invention is to provide novel pharmaceutical unit dosage forms containing naphthoquinone derivatives which inhibit the growth of cancer cells when administered to mammals in need thereof, including human cancer patients in need thereof.

A further aim of the present method is to provide a chemotherapeutic treatment for the inhibition of cancer in mammals, including humans.

Further aims, objects, and advantages of the presently described methods and products will become clear upon a complete reading of the following Detailed Description, drawings, and attached claims.

DETAILED DESCRIPTION OF THE INVENTION

Figure 1:
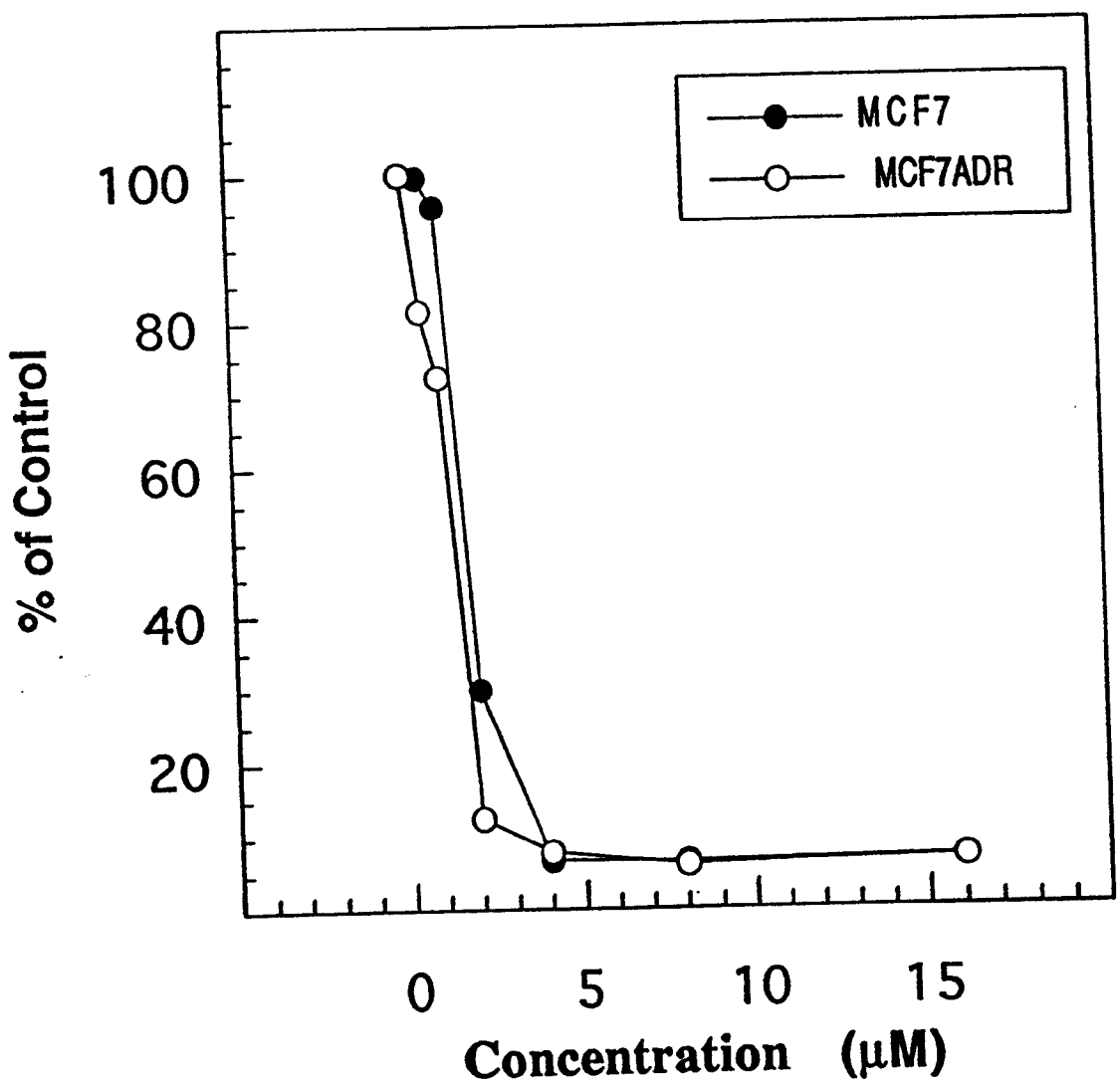
FIG. 1 is a graph showing the in vitro effect of increasing concentrations of 4-pentyloxy-1,2-napthoquinone on the survival of cultured MCF7 (ATCC HTB-22) breast cancer cells (●) and adriamycin-resistant MCF7 breast cancer cells (MCF7ADR) (○).

At the core of the present invention is a method for the inhibition of neoplastic cell growth utilizing 4-substituted-1,2-naphthoquinones and the compounds used in the method. More specifically still, the invention is a method for the inhibition of the growth of neoplastic cells, including neoplastic cell lines which are resistant to the cytotoxic effects of adriamycin, daunorubicin, teniposide, and other chemotherapeutic agents.

I. Definitions

As used herein, the following terms shall have the meanings provided. All other terms not specifically defined herein shall be given their common and accepted definitions as used by those skilled in the relevant art:

The terms "cancer," "cancer cell(s)," and "neoplasm(s)" are synonymous and refer to all types of cancer, including both benign and malignant tumors and neoplasms, without limitation. This includes melanomas, lymphomas, leukemias, sarcomas, and the like. Illustrative examples of cancerous tumors and tissues are cutaneous tumors, such as malignant melanomas and mycosis fungoides; hematologic tumors, such as leukemias, for example, acute lymphoblastic, acute myelocytic or chronic myelocytic leukemia; lymphomas, such as Hodgkin's disease or malignant lymphoma; gynecologic tumors, such as ovarian and uterine tumors; urologic tumors, such as those of the prostate, bladder, or testis; soft tissue sarcomas, osseus or non-osseus sarcomas, breast tumors; tumors of the pituitary, thyroid, and adrenal cortex; gastrointestinal tumors, such as those of the esophagus, stomach, intestine, and colon; pancreatic and hepatic tumors; laryngeae papillomestasas, brain and other CNS tumors, and lung tumors.

"ADR-resistant" designates cancer cells which are resistant to the antineoplastic drug referred to as adriamycin and other antineoplastic drugs which share the same skeletal structure as adriamycin, such as daunorubicin and teniposide. Although now generally referred to in the literature as doxorubicin (and also known as adriablastina), because the term "adriamycin" is still commonly used, it shall be used herein. "ADR" shall be used to designate adriamycin itself. Adriamycin, daunorubicin, and teniposide are cytotoxic agents believed to exert their cytotoxicity via their ability to intercalate into DNA. ADR-resistant cells are those cells which are specifically resistant to the cytotoxicity of adriamycin, and which may have some degree of resistance to daunorubicin or other chemotherapeutic compounds. The systematic name of adriamycin is (8S-cis)-10{(3-amino-2,3,6-trideoxy-α-L-lyxo-hexapyranosyl)oxy}-7,8,9,10tetrahydro-6,8,11-trihydroxy-8-(hydroxyacetyl)-1-methoxy-5,12-naphthacenedione.

Structurally, adriamycin, daunorubicin, and teniposide appear as follows:

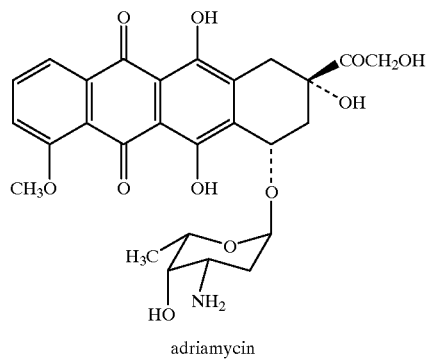

adriamycin

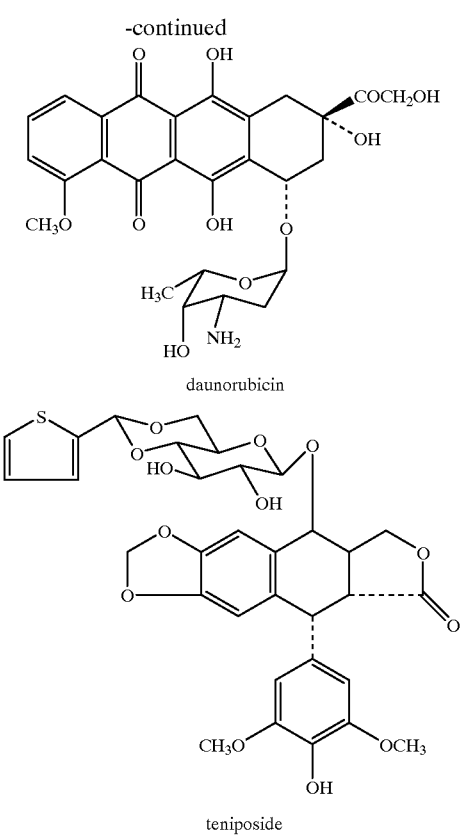

daunorubicin teniposide

"MDR" refers to multi-drug resistant cancer cells. As defined herein, these cancers are neoplastic cells are resistant to all chemotherapeutic agents now commonly used in the chemical treatment of cancers.

"Merbarone" is the common name given to 5-(N-phenylcarboxamido)-2-thiobarbituric acid.

"Inhibiting cell growth" means slowing, interrupting, arresting, and/or terminating the growth, proliferation, and/or metastases of a rapidly proliferating cancer cell or cancerous cell line. It is understood that inhibiting cell growth of a cancer cell or cell line does not necessarily provide a "cure" in the sense that the tumor tissue or transformed cells are completely destroyed.

II. Synthesis of 4-Substituted-1,2-Napthoquinones

The compounds described herein may be prepared using the reactions, techniques, and general synthetic procedures described herein below. Each of the references cited below are incorporated herein by reference. The various reactions may be performed in several solvents which are appropriate to the reagents and materials employed and which are suitable for the transformation being effected. It is understood by those skilled in the art of organic synthesis that the functionality present on portions of a given molecule must be compatible with the reagents and reaction conditions proposed.

Synthesis of the present compounds can be accomplished using standard literature methodologies. The starting materials, 1,2-naphthoquinone and 2-hydroxy-1,4-naphthoquinone (lawsone), and all required reagents are widely available from several international commercial suppliers, including the Sigma Chemical Company (St. Louis, Miss., USA).

A. Preparation of 4-alkoxy-1,2-naphthoquinones: The synthesis of 4-alkoxy-1,2-naphthoquinones proceeds via the silver salt of 2-hydroxy-1-4-naphthoquinone (lawsone). The preferred synthesis is that described by L. F. Fieser (1926 and 1927). An equally suitable synthesis is described by Takuwa et al. (1986). An illustrative synthesis, showing the preparation of 4-isopropoxy-1,2-naphthoquinone, proceeds as follows:

To 750 mL of hot water was added 50.0 g (0.287 mol) of 2-hydroxy-1,4-naphthoquinone. Sufficient ammonium hydroxide was added to bring the quinone into solution. Then 287 mL of 1 M AgNO$_3$ was added, and the mixture was cooled in an ice-bath. The red salt was collected by filtration and washed successively with water, ethanol, and diethyl ether and dried. Yield: 76.13 g (94%) of silver salt.

To a suspension of 5.00 g (17.8 mmol) of the silver salt of 2-hydroxy-1,4-naphthoquinone in 50 mL of benzene was added 1.85 mnL (19.7 mmol) of 2-bromopropane. The reaction mixture was heated at 50° C. for 24 hr. The benzene was removed under reduced pressure. The crude material was treated with ethyl acetate to dissolve the organic products, and the resultant solution was filtered to remove silver salts. The ethyl acetate solution was extracted first with cold 10% NH$_4$OH until the extract was colorless, and then with 5% NaHSO$_3$ until the extract gave no precipitate of orthoquinone upon addition of Na$_2$CO$_3$ solution. The NaHSO$_3$ extracts were combined, treated with Na$_2$CO$_3$ solution, and extracted with CH$_2$Cl$_2$. The CH$_2$Cl$_2$ extracts were combined and dried with MgSO$_4$. Removal of solvent yielded 2.03 g (53%) of 4-(sopropoxy-1,2-naphthoquinone, which was recrystallized from benzene-ligroin: mp 125–125.5° C. $^1$H NMR (300 MHz, CDCl$_3$, TMS) δ 8,12 (dd, J=8.1 Hz, 1H), 7.89 (dd, J=8.1 Hz, 1H), 7.69 (td, J=8.1 Hz, 1H), 7.59 (td, J=8.1 Hz, 1H), 5.96 (s, 1H), 4.75 (septet, J=6 Hz, 1H), 1.49 (d, J=6 Hz, 6H); $^{13}$C NMR (75.5 MHz, CDCl$_3$, TMS) δ 179.5, 179.3, 166.7, 134.8, 132.3, 131.3, 130.4, 128.6, 124.8, 103.7, 72.9, 21.4. Analysis calculated for C$_{13}$H$_{12}$O$_3$: C=72.20, H=5.60; Found: C=72.06, H=5,62.

B. Preparation of 4-thio-1,2-naphthoquinones: The synthesis of the thiols of Formula I can be effected using the method of Mackenzie et al. (1986). An illustrative synthesis for the preparation of 4-pentanethio-1,2-naphthoquinone, proceeds as follows:

To a solution of 1.00 g (6.32 mmol) of 1,2-naphthoquinone in 150 mL of methanol was added 784 μL (6.32 mmol) of pentanethiol. The reaction mixture was stirred at room temperature for 22 hr. Removal of the methanol and column chromatography on silica gel with CH$_2$Cl$_2$ afforded 104.2 mg (6%) of 4-pentanethio-1,2-naphthoquinone, which was recrystallized from hexanes: mp 107–108° C. $^1$H NMR (300 MHz, CDCl$_3$, TMS) δ 8.17 (d, J=7.7 Hz, 1H), 7.85 (d, J=7.7 Hz, 1H), 7.68 (t, J=7.7 Hz, 1H), 7.57 (t, J=7.7 Hz, 1H), 6.42 (s, 1H), 3.04 (t, J=7 Hz, 2H), 1.9–1.8 (m, 2H), 1.5–1.3 (m, 4H), 0.95 (t, J=7 Hz, 3H); $^{13}$C NMR (75.5 MHz, CDCl$_3$, TMS) δ 179.6, 176.2, 160.2, 134.9, 133.7, 131.1, 130.4, 129.2, 125.2, 119.7, 31.8, 31.1, 27.2, 22.2, 13.8. Analysis calculated for C$_{15}$H$_{16}$O$_2$S: C=69.19, H=6.21, S=12.31; Found C=68.97, H=6.22, S=12.31.

C. Preparation of 4-amino-1,2-naphthoquinones: The amino derivatives can be obtained via reaction of the alkoxy derivatives with an appropriate amine. The preferred synthetic route is that described by L. F. Fieser (1935). An illustrative synthesis of 4-pentylamino-1,2-naphthoquinone proceeds as follows:

To a stirred suspension of 650 mg (3.45 mmol) of 4-methoxy-1,2-naphthoquinone in 20 mL of ethanol was added 0.80 mL (6.90 mmol) of pentylamine. The reaction mixture was stirred at room temperature for 60 min. The resulting red precipitate was collected by filtration and then triturated with 20 mL of ethyl acetate to afford 411.7 mg (49%) of 4-pentylamino-1,2-naphthoquinone, which was recrystallized from ethyl acetate: mp>215° C.; $^1$H NMR (300 MHz, CDCl$_3$, TMS) δ 8.21 (dd, J=7.5, 1.6 Hz, 1H), 7.69 (td, J=7.7, 1.6 Hz, 1H), 7.61 (t, J=7.5 Hz, 1H), 7.49 (d, J=7.9 Hz, 1H), 5.86 (s, 1H), 5.76 (br s, 1H), 3.4–3.3 (m, 2H), 1.8–1.7 (m, 4H), 1.5–1.4 (m, 4H), 0,95 (t, J=7 Hz, 3H); $^{13}$C NMR (75.5 MHz, d$_6$-DMSO, TMS) δ 182.0, 174.7, 154.8, 134.1, 131.2, 130.8, 127.8, 123.3, 98.0, 43.1, 28.7, 27.4, 21.8, 13.9. Analysis calculated for C$_{15}$H$_{17}$NO$_2$: C=74.04, H=7.06, N=5.7; Found: C=73.88, H=7.01, N=5.73.

III. Administration and Pharmaceutical Dosage Forms:

The above-described compounds being effective to inhibit the growth of cancer cells, the compounds are suitable for the therapeutic treatment of neoplastic conditions in mammals, including humans. Cancer cell growth inhibition at pharmacologically-acceptable concentrations has been shown in human breast cancer, colon cancer, lung cancer, brain cancer, and prostate cancer cell lines.

Administration of the subject naphthoquinones to a human or non-human patient can be accomplished by any means known. The preferred administration route is parenteral, including intravenous administration, intraarterial administration, intratumor administration, intramuscular administration, intraperitoneal administration, and subcutaneous administration in combination with a pharmaceutical carrier suitable for the chosen administration route. The treatment method is also amenable to oral administration.

It must be noted, as with all pharmaceuticals, the concentration or amount of the 4-substituted-1,2-naphthoquinone administered will vary depending upon the severity of the ailment being treated, the mode of administration, the condition and age of the subject being treated, and the particular naphthoquinone or combination of naphthoquinones being used.

The compounds described herein are administratable in the form of tablets, pills, powder mixtures, capsules, injectables, solutions, suppositories, emulsions, dispersions, food premixes, and in other suitable forms. The pharmaceutical dosage form which contains the compounds described herein is conveniently admixed with a non-toxic pharmaceutical organic carrier or a non-toxic pharmaceutical inorganic carrier. Typical pharmaceutically-acceptable carriers include, for example, mannitol, urea, dextrans, lactose, potato and maize starches, magnesium stearate, talc, vegetable oils, polyalkylene glycols, ethyl cellulose, poly (vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical dosage form may also contain non-toxic auxiliary substances such as emulsifying, preserving, or wetting agents, and the like.

Solid forms, such as tablets, capsules and powders, can be fabricated using conventional tabletting and capsule-filling machinery, which is well known in the art. Solid dosage forms may contain any number of additional non-active ingredients known to the art, including excipients, lubricants, dessicants, binders, colorants, disintegrating agents, dry flow modifiers, preservatives, and the like.

Liquid forms for ingestion can be formulated using known liquid carriers, including aqueous and non-aqueous carriers, suspensions, oil-in-water and/or water-in-oil emulsions, and the like. Liquid formulation may also contain any number of additional non-active ingredients, including colorants, fragrance, flavorings, viscosity modifiers, preservatives, stabilizers, and the like.

For parenteral administration, the compounds of Formula I may be administered as injectable dosages of a solution or suspension of the compound in a physiologically-acceptable diluent or sterile liquid carrier such as water or oil, with or without additional surfactants or adjuvants. An illustrative list of carrier oils would include animal and vegetable oils (peanut oil, soy bean oil), petroleum-derived oils (mineral oil), and synthetic oils. In general, for injectable unit doses, water, saline, aqueous dextrose and related sugar solutions, and ethanol and glycol solutions such as propylene glycol or polyethylene glycol are preferred liquid carriers.

The pharmaceutical unit dosage chosen is preferably fabricated and administered to provide a concentration of drug at the point of contact with the cancer cell of from 1 $\mu$M to 10 mM. More preferred is a concentration of from 1 to 100 $\mu$M. This concentration will, of course, depend on the chosen route of administration and the mass of the subject being treated.

IV. Biological Activity of the 4-Substituted o-Naphthoquinones Against Neoplastic Cells Of great significance in the present invention is the utility of the described naphthoquinones to inhibit the growth and proliferation of neoplastic cells. Further still, in standard in vitro testing, the naphthoquinones described herein induce cell death in several neoplastic cell lines at drug concentrations smaller than 10 $\mu$M. In serial dilution, in vitro studies, the naphthoquinones of the present invention have been shown to cause cell death in accepted in vitro test cultures for human breast cancer, lung cancer, colon cancer, brain cancer, and prostate cancer at minute concentrations heretofore undescribed in the scientific literature.

Examples 1–14 below, and the accompanying Figures, illustrate a series of experiments designed to illustrate the ability of the subject o-naphthoquinones to induce cell death in several different neoplastic cell lines. Each graph has as its X-axis the concentration of the particular compound being tested. The Y-axis of each graph is a linear scale representing the fraction of cell survival in each of the cultures tested. A standardized protocol was used throughout all of the test cultures.

As specifically detailed in the Examples, the compounds of Formula I, wherein R is pentyloxy, 2-methyl-propyloxy, 3-methyl-butyloxy, isopropyloxy, 2-butenyloxy, benzyloxy, cyclohexylmethyloxy, 2-pentenyloxy, n-heptyloxy, n-pentylthio, and N,N-dimethylamino-ethylamino were shown to be highly effective in inhibiting cancer cell growth in MCF7 human breast cancer cells at concentrations well below 10 $\mu$M, and in some instances less than 5 $\mu$M.

Furthermore, the 4-substituted-1,2-napthoquinones of Formula I display equally lethal effects in several other cancer cell lines. The subject compounds display similar cytotoxic effects against human leukemias, including CEM, CEM/VM-1 (teniposide-resistant), and CEM/M70-B1 (merbarone-resistant) cell lines, as well as HL60 and HL6 ADR (adriamycin-resistant) leukemia cell lines; human lung cancer cells including A549 cells, human colon cancer cells including HT29 cells (ATCC HTB-38), and human epidermoid cancer cells including KB3-1 (ATCC CCL-17), KBH-1, and its multi-drug resistant variant KB-V1 (vinblastine-resistant). The compounds are also effective to inhibit the growth of non-human cancers, including the metastatic rat prostate cell line AT3.1.

V. Biological Activity Against ADR-Resistant and MDR-Resistant Neoplastic Cells

It is well known that multiple-drug resistance (MDR) can be induced in neoplastic cells by anthracyclin quinones and quinoid-forming etoposides. In particular, the resistance of MCF7ADR cells is due to two distinct mechanisms. The first mechanism involves an ATP-driven efflux pump, and is known as the P-glycoprotein mechanism; the second mechanism involves an altered glutathione cycle.

KB-V1, a human epidermoid cancer cell line, is resistant to vinblastine, a known P-glycoprotein substrate. However, when exposed to the 4-substituted-1,2-naphthoquinones of Formula I, KB-V1 cells were killed to the same extent as were non-resistant KB-3-1 parent cells. This indicates that the subject compounds are not substrates for the P-glycoprotein efflux pump. Moreover, in a comptetive binding assay using $^{125}$NAS-VP, a photoaffinity analog of verapamil, the binding of $^{125}$NAS-VP to P-glycoprotein was not inhibited by up to 100 $\mu$M of the 4-substituted-1,2-naphthoquinones of Formula I. This lends support to the thought that the Formula I compounds are not exported from MDR cells via the P-glycoprotein efflux pump.

It does appear that the altered glutathione pathway of MDR cells plays a role in the cytotoxic effect of the subject compounds. When MCF7 and MCF7ADR cells were cultured in the presence of the Formula I compounds and L-butathione sulfoximine (BSO), a glutathione synthetase inhibitor, the sensitivity of MCF7ADR cells to the subject compounds increased by approximately three-fold. The cytotoxicity of the compounds against the MCF7 cells remained the same when treated with BSO. However, when treated with the subject compounds in the absence of BSO, the sensitivity of MCF7ADR cells was approximately the same as the sensitivity of MCF7 cells.

In short, treating ADR-resistant cells with a compound of Formula I revealed that there is no cross-resistance to the subject compounds.

The compounds of Formula I are also effective against cells which are resistant to topoisomerase II inhibitors. The human acute leukemia cell line CEMIVM-1 is resistant to teniposide (a topoisomerase-ATP dependent compound) and CEM/M70-B1 is resistant to merbarone (a topoisomerase II inhibitor). The subject 4-substituted-1,2-naphthoquinones were equally lethal to all CEM cells lines, including the parent type.

EXAMPLES

The following Examples are provided solely to aid in a clear understanding of the presently claimed invention. The following Examples do not limit the scope of the invention described above or claimed herein in any fashion.

Standard Protocol:

For each of the in vitro tests whose results are described in Examples 1 through 13, the following standard protocol was followed:

Day 1:

10 standard culture flasks for each drug to be tested are plated with $5 \times 10^5$ cells of a given type in 5 mL of media and allowed to incubate for 16–24 hours at 37° C.

Cell Lines and Media:

Human breast cancer cell lines MCF7, MCF7ADR (adriamycin-resistant), and MCF7GPX (expressing high levels of glutathione peroxidase) were grown in Richter's Improved Modified Eagle's Medium supplemented with 10% fetal bovine serum (FBS) and 2.2 g/L sodium bicarbonate. Human leukemia cell lines CEM, CEM/VM-1 (teniposide-resistant), and CEM/M70-B1 (merbarone-resistant) were grown in RPMI medium supplemented with 10% FBS and 2 mM L-glutathione. Human lung cancer cell line A549 was grown in Ham's F-12K medium supplemented with 10% FBS and 2 mM L-glutathione. Human colon cancer cell line HT29 was grown in Dubecco's Modified Eagle's Medium supplemented with 10% FBS and 2 mM L-glutamine. Metastatic rat prostate cell line AT3.1 was grown in RPMI medium supplemented with 8% FBS. Human leukemia cell lines HL60 and HL60ADR were grown in PRMI medium supplemented with 10% FBS. Human epidermoid cancer cell line KB-3-1 and its multi-drug resistant variant KB-V1 (vinblastine-resistant) were grown in Dulbecco's Modified Eagle's Medium supplemented with 10% FBS.

The CEM cell lines were cultured in antibiotic-free medium. The HT29 cell line was cultured in 50 µg/mL gentamycin. The remaining cell lines were cultured in 100 units/mL penicillin and 100 µg/mL streptomycin. All cell cultures were maintained at 37° C. in 5% $CO_2$/95% humidified air.

Day 2:

Fresh stocks of the compounds to be evaluated are prepared in sterile DMSO. For each drug, two of the ten culture flasks prepared on Day 1 are used as controls. The control flasks are treated with DMSO only. Four flasks for each compound are then treated with serially-diluted concentrations of the compound (1, 5, 10, 50 µm or 2, 10, 20, 100 µm). The remaining flasks are left untouched. The cells are incubated for 4 hours at 37° C.

After 4 hours the control flasks are counted (2 counts for each flask) and the cells per mL calculated based on the average of the control counts. The cells are then replated into six 60 mm dishes for each flask from dilutions based on the cells/mL of the control. (In the various test runs, cell concentrations ranged from approximately 50 to approximately 800 cells per mL.)

Day 15–20:

The cells are monitored for colony formation. When visible, the cells are stained with 0.5% crystal violet (in 95% EtOH) and counted. The plating efficiency for each dish is then calculated. The plating efficiencies of the six dishes for each flask are averaged and the standard deviation is calculated. The fraction of cell survival at each concentration is determined based on the controls and plotted as log fraction of cell survival±standard deviation versus the dose of the compound.

Example 1

4-Pentyloxy-1,2-napthoquinone Against MCF7 Cells and Adriamycin-Resistant MCF7 Cells Following the standard protocol, the survival of cultured human breast cancer cells MCF7 and adriamycin-resistant MCF7 cells in the presence of increasing concentrations of 4-pentyloxy-1,2-napthoquinone was investigated. The results of both studies are depicted in FIG. 1. The plots for the survival of cultured MCF7 breast cancer cells (●) and adriamycin-resistant MCF7 breast cancer cells (MCF7ADR) (○) as shown in FIG. 1 are virtually identical. At a concentration of less than 5 µM, 4-pentyloxy-1,2-napthoquinone effectively and equally inhibits the growth of both MCF7 and MCF7ADR cells in culture.

Example 2

Figure 2:
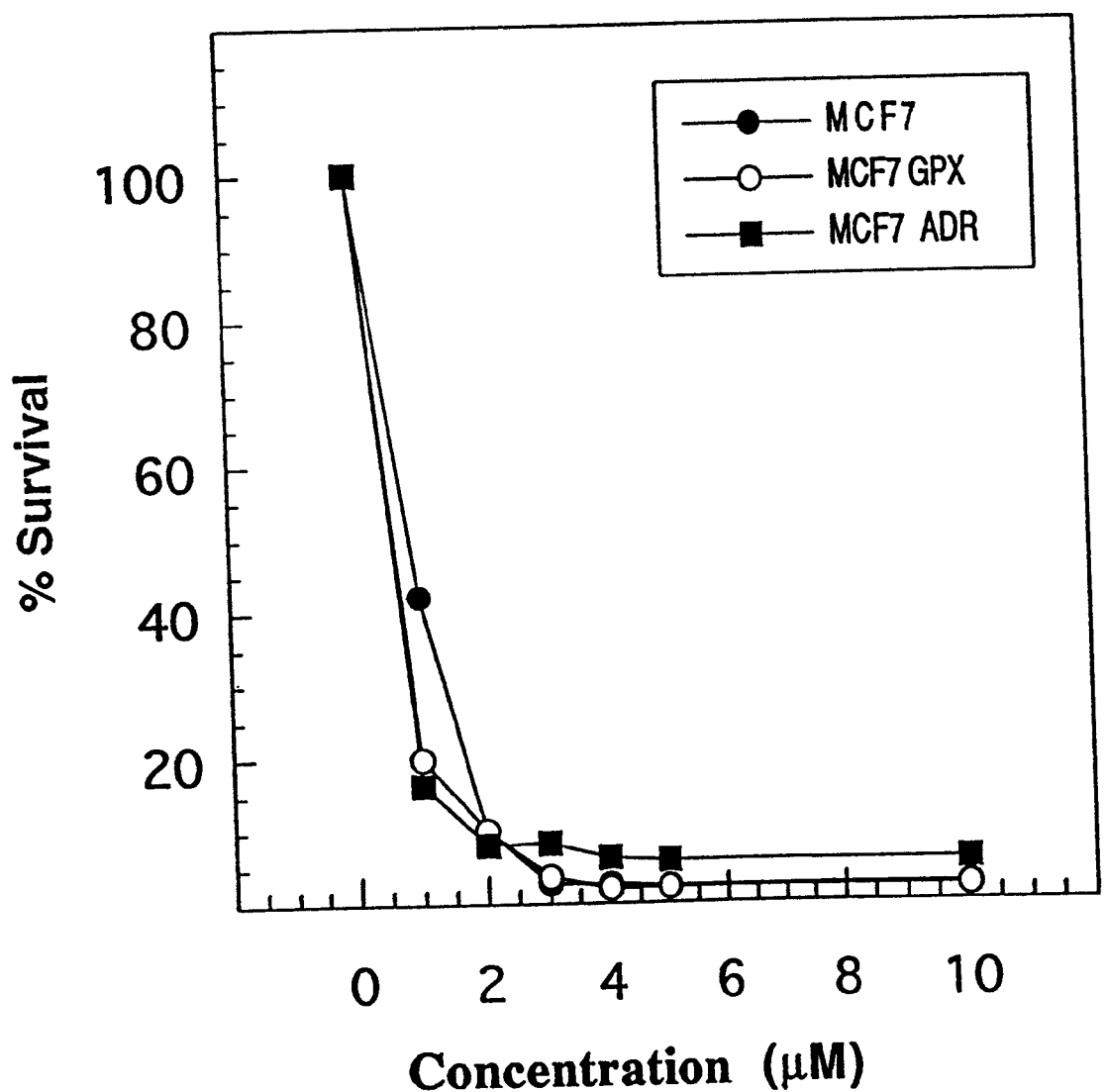
FIG. 2 is a graph showing the in vitro effect of increasing concentrations of 4-pentyloxy-1,2-napthoquinone on the survival of cultured MCF7 breast cancer cells (●), adriamycin-resistant MCF7 breast cancer cells (MCF7ADR) (■), and MCF7 breast cancer cells containing a high level of cDNA-expressed glutathione peroxidase (MCF7GPX) (○).

4-Pentyloxy-1,2-napthoquinone Against MCF7 Cells, Adriamycin-Resistant MCF7 Cells, and MCF7 Cells Expressing High Levels of Glutathione Peroxidase Following the standard protocol, the survival of cultured human breast cancer cells MCF7, adriamycin-resistant MCF7 cells, and MCF7 breast cancer cells containing a high level of cDNA-expressed glutathione peroxidase (MCF7GPX), in the presence of increasing concentrations of 4-pentyloxy-1,2-napthoquinonewas investigated. The results of all three studies are depicted in FIG. 2. As in Example 1, the plots for the survival of cultured MCF7 breast cancer cells (●), adriamycin-resistant MCF7 breast cancer cells (MCF7ADR) (■), and MCF7 breast cancer cells containing a high level of cDNA-expressed glutathione peroxidase (MCF7GPX) (○) as shown in FIG. 2 are virtually identical. At concentrations of approximately 3 µM, 4-pentyloxy-1,2-napthoquinone effectively and equally inhibits the growth of MCF7, MCF7ADR, and MCF7GPX cells in culture.

Example 3

Figure 3:
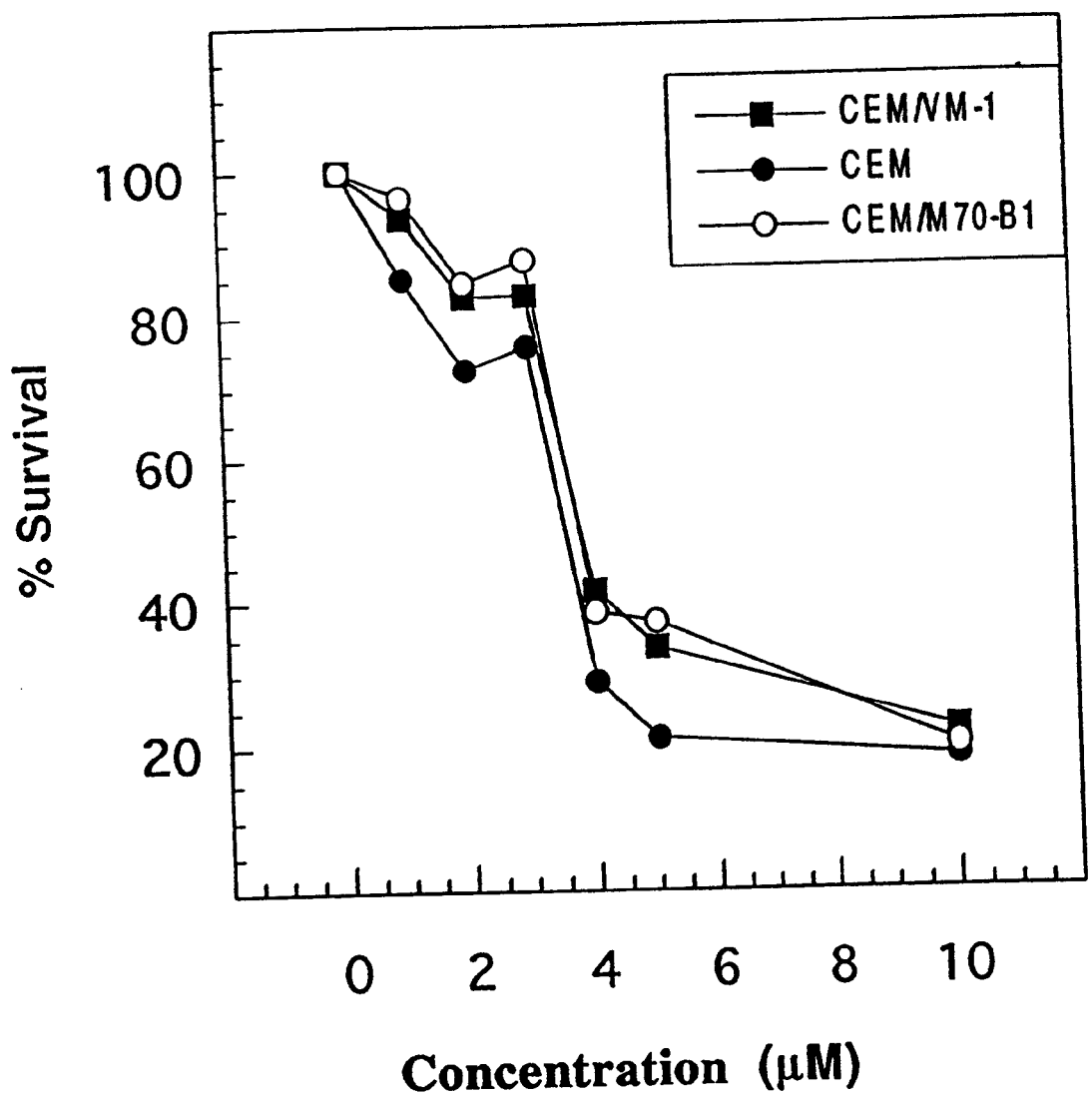
FIG. 3 is a graph showing the in vitro effect of increasing concentrations of 4-pentyloxy-1,2-napthoquinone on the survival of cultured CEM leukemia cells (ATCC CCL-119) (●), teniposide-resistant CEM leukemia cells (CEM-VM-1) (■), and merbarone-resistant leukemia cells (CEM/M70-B1) (○).

4-Pentyloxy-1,2-napthoquinone Against CEM Leukemia Cells, Teniposide-Resistant CEM Leukemia and Merbarone-Resistant Leukemia Following the standard protocol, the survival of cultured CEM leukemia cells, teniposide-resistant CEM leukemia cells (CEM-VM-1), and merbarone-resistant leukemia cells (CEM/M70-B1) (○) in the presence of increasing concentrations of 4-pentyloxy-1,2-napthoquinone was investigated. The results of the three studies are depicted in FIG. 3. As in the previous two Examples, the plots for the survival of cultured CEM leukemia cells (●), teniposide-resistant CEM leukemia cells (CEM-VM-1) (■), and merbarone-resistant leukemia cells (CEM/M70-B1) (○) are virtually identical and show effective inhibition of cell growth in both CEM cells and drug-resistant CEM cells in culture.

Example 4

Figure 4:
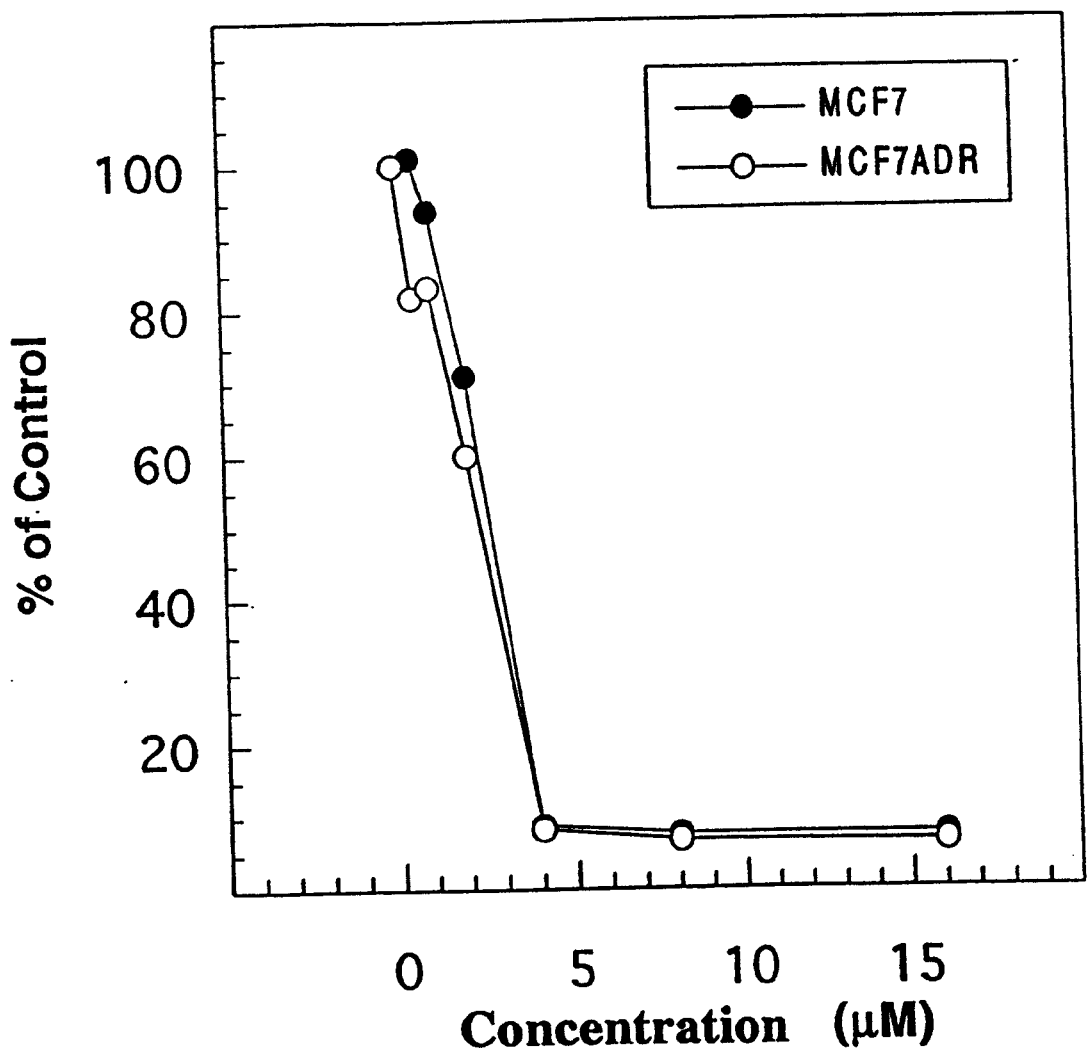
FIG. 4 is a graph showing the in vitro effect of increasing concentrations of 4-(2-methyl-propyloxy)-1,2-napthoquinone on the survival of cultured MCF7 breast cancer cells (●) and adriamycin-resistant MCF7 breast cancer cells (MCF7ADR) (○).

4-(2-Methyl-propyloxy)-1,2-napthoquinone Against MCF7 Cells and Adriamycin-Resistant MCF7 Cells Following the standard protocol, the survival of cultured human breast cancer cells MCF7 and adriamycin-resistant MCF7 cells in the presence of increasing concentrations of 4-(2-methyl-propyloxy)-1,2-napthoquinone was investigated. The results of both studies are depicted in FIG. 4. The plots for the survival of cultured MCF7 breast cancer cells (●) and adriamycin-resistant MCF7 breast cancer cells (MCF7ADR) (○) are identical. At a concentration of less than 5 µM, 4-(2-methyl-propyloxy)-1,2-napthoquinone effectively and equally inhibits the growth of both MCF7 and MCF7ADR cells in culture.

Example 5

Figure 5:
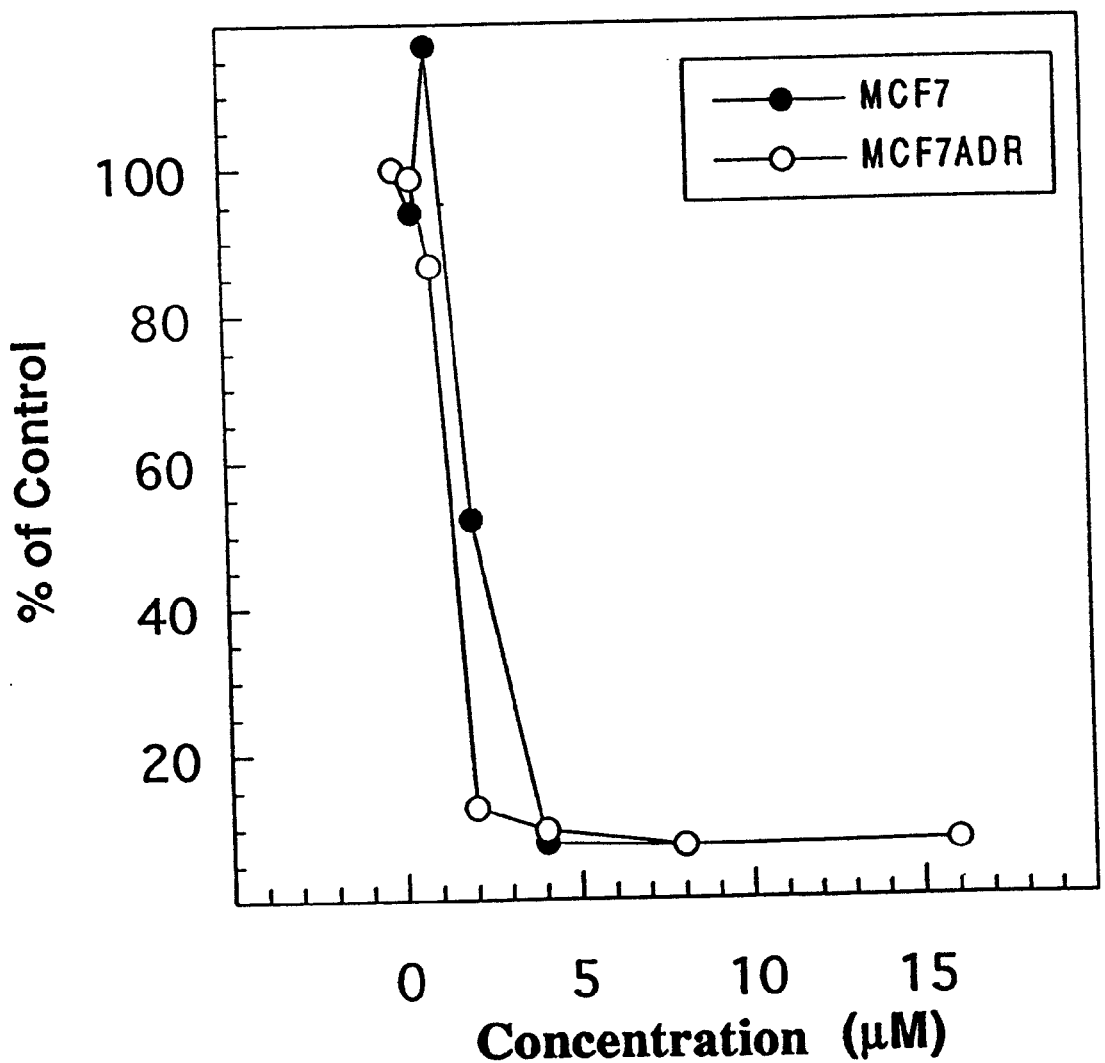
FIG. 5 is a graph showing the in vitro effect of increasing concentrations of 4-(3-methyl-butyloxy)-1,2-napthoquinoneon the survival of cultured MCF7 breast cancer cells (●) and adriamycin-resistant MCF7 breast cancer cells (MCF7ADR) (○).

4-(3-Methyl-butyloxy)-1,2-napthoquinone Against MCF7 Cells and Adriamycin-Resistant MCF7 Cells Following the standard protocol, the survival of cultured human breast cancer cells MCF7 and adriamycin rresistant MCF7 cells in the presence of increasing concentrations of 4-(3-methyl-butyloxy)-1,2-napthoquinonewas investigated. The results of both studies are depicted in FIG. 5. The plots depict the survival of cultured MCF7 breast cancer cells (●) and adriamycin-resistant MCF7 breast cancer cells (MCF7ADR) (○) in the presence of 4-(3-methyl-butyloxy)-1,2-napthoquinone. At a concentration of less than 5 µM, 4-(3-methyl-butyloxy)-1,2-napthoquinoneeffectively and equally inhibits the growth of both MCF7 and MCF7ADR cells in culture.

Example 6

Figure 6:
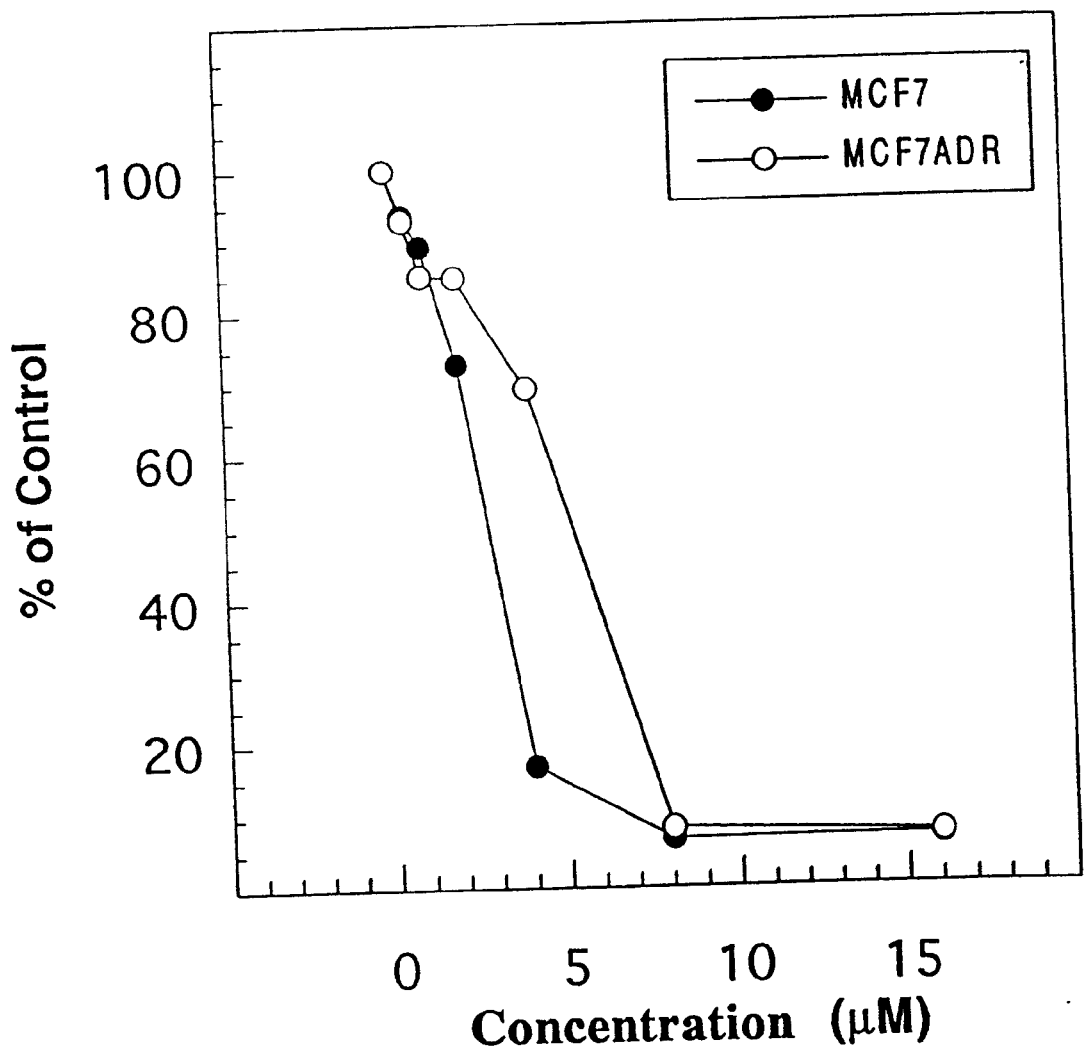
FIG. 6 is a graph showing the in vitro effect of increasing concentrations of 4-(isopropyloxy)-1,2-napthoquinone on the survival of cultured MCF7 breast cancer cells (●) and adriamycin-resistant MCF7 breast cancer cells (MCF7ADR) (○).

4-(Isopropyloxy)-1,2-napthoquinone Against MCF7 Cells and Adriamycin-Resistant MCF7 Cells Following the standard protocol, the survival of cultured human breast cancer cells MCF7 and adriamycin-resistant MCF7 cells in the presence of increasing concentrations of 4-(isopropyloxy)-1,2-napthoquinone was investigated. The results of both studies are depicted in FIG. 6. The plots depict the survival of cultured MCF7 breast cancer cells (●) and adriamycin-resistant MCF7 breast cancer cells (MCF7ADR) (○). At a concentration of about 8 μM, 4-(isopropyloxy)-1,2-napthoquinone effectively and equally inhibits the growth of both MCF7 and MCF7ADR cells in culture.

Example 7

Figure 7:
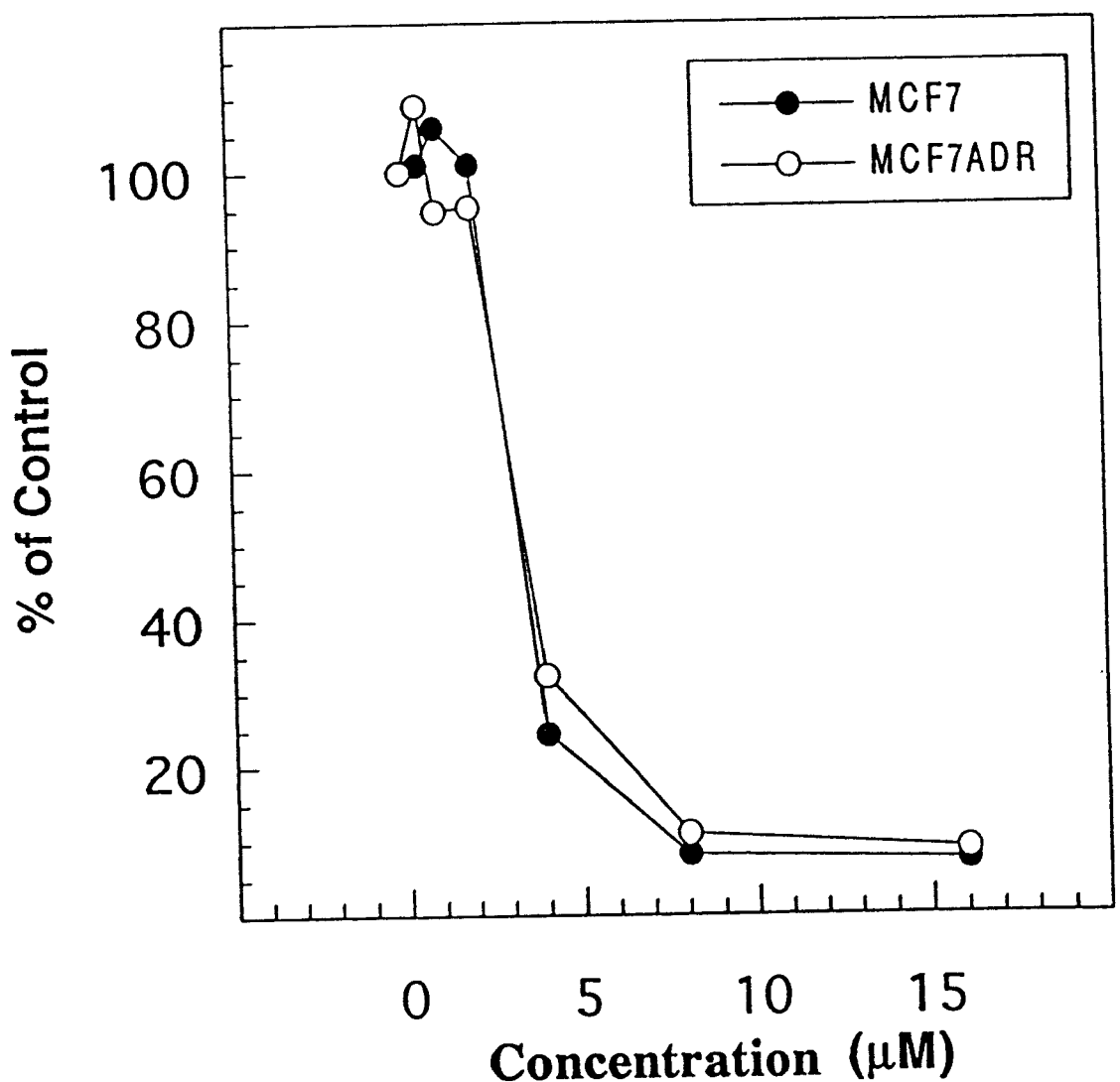
FIG. 7 is a graph showing the in vitro effect of increasing concentrations of 4-(2-butenyloxy)-1,2-napthoquinone on the survival of cultured MCF7 breast cancer cells (●) and adriamycin-resistant MCF7 breast cancer cells (MCF7ADR) (○).

4-(2-Butenyloxy)-1,2-napthoquinone Against MCF7 Cells and Adriamycin-Resistant MCF7 Cells Following the standard protocol, the survival of cultured human breast cancer cells MCF7 and adriamycin-resistant MCF7 cells in the presence of increasing concentrations of 4-(2-butenyloxy)-1,2-napthoquinone was investigated. The results of both studies are depicted in FIG. 7. The plots depict the survival of cultured MCF7 breast cancer cells (●) and adriamycin-resistant MCF7 breast cancer cells (MCF7ADR) (○). At a concentration of about 8 μM, 4-(2-butenyloxy)-1,2-napthoquinone effectively and equally inhibits the growth of both MCF7 and MCF7ADR cells in culture.

Example 8

Figure 8:
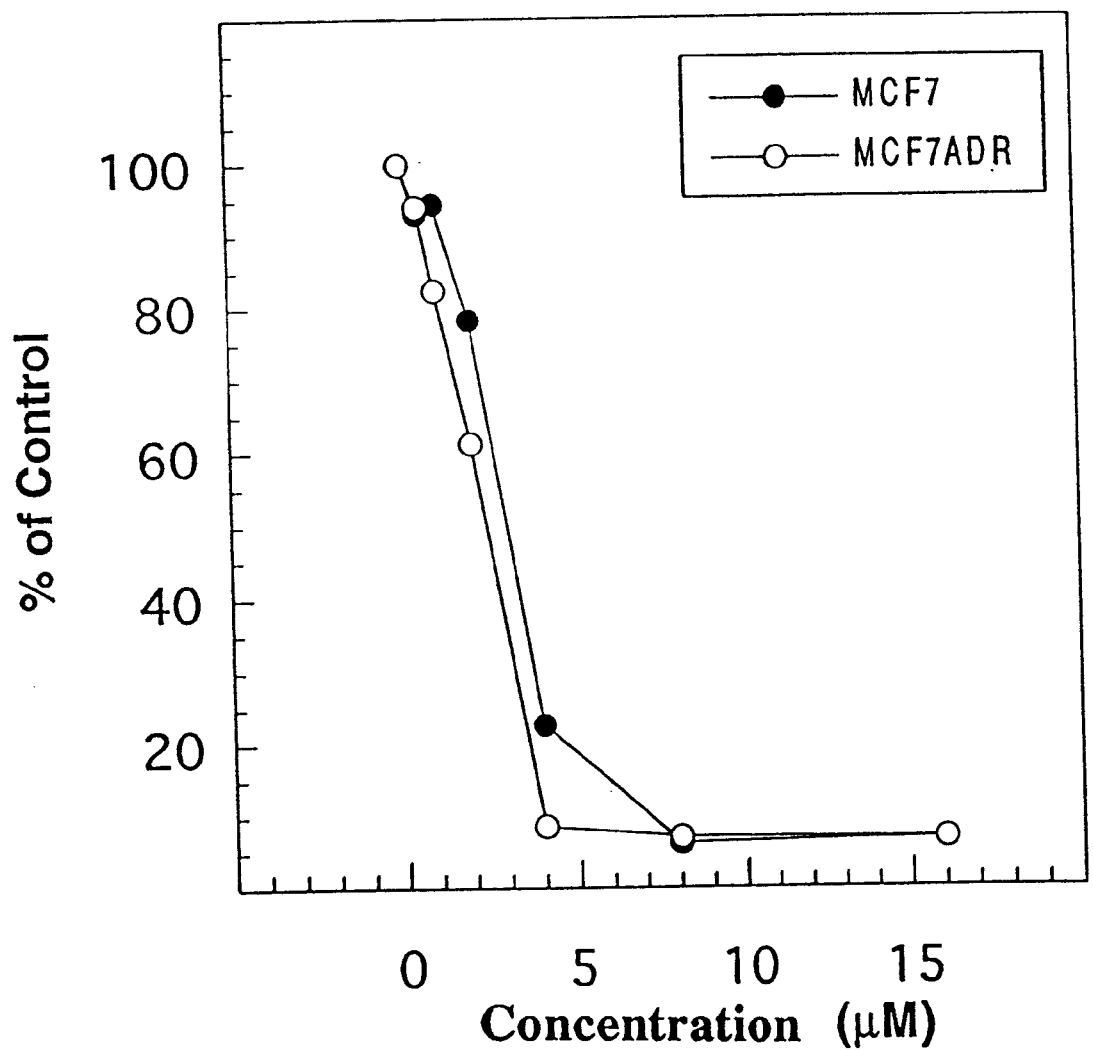
FIG. 8 is a graph showing the in vitro effect of increasing concentrations of 4-benzyloxy-1,2-napthoquinone on the survival of cultured MCF7 breast cancer cells (●) and adriamycin-resistant MCF7 breast cancer cells (MCF7ADR) (○).

4-Benzyloxy-1,2-napthoquinone Against MCF7 Cells and Adriamycin-Resistant MCF7 Cells Following the standard protocol, the survival of cultured human breast cancer cells MCF7 and adriamycin-resistant MCF7 cells in the presence of increasing concentrations of 4-benzyloxy-1,2-napthoquinone was investigated. The results of both studies are depicted in FIG. 8. The plots depict the survival of cultured MCF7 breast cancer cells (●) and adriamycin-resistant MCF7 breast cancer cells (MCF7ADR) (○).

Example 9

Figure 9:
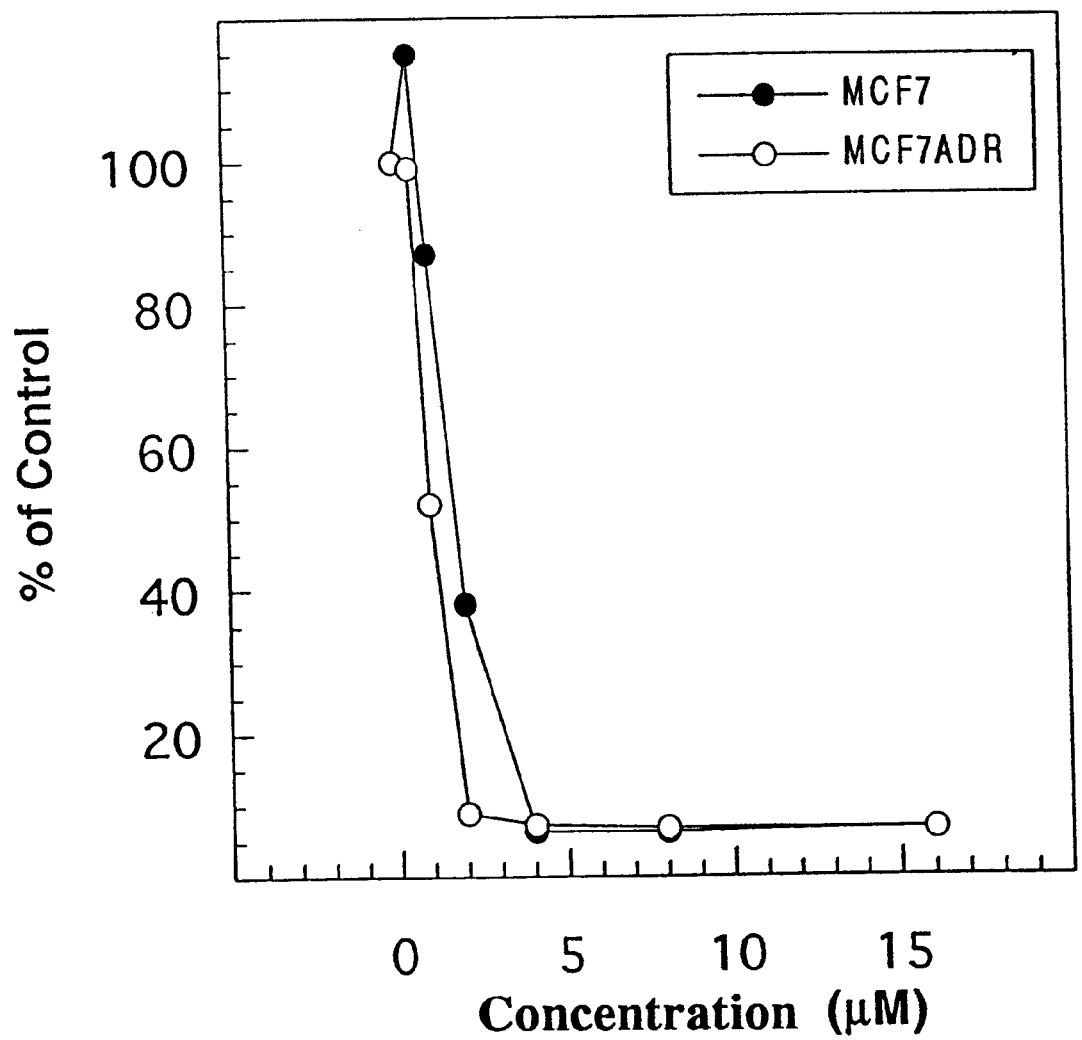
FIG. 9 is a graph showing the in vitro effect of increasing concentrations of 4-cyclohexylmethyloxy-1,2-napthoquinone on the survival of cultured MCF7 breast cancer cells (●) and adriamycin-resistant MCF7 breast cancer cells (MCF7ADR) (○).

4-Cyclohexylmethyloxy-1,2-napthoquinone Against MCF7 Cells and Adriamycin-Resistant MCF7 Cells Following the standard protocol, the survival of cultured human breast cancer cells MCF7 and adriamycin-resistant MCF7 cells in the presence of increasing concentrations of 4-cyclohexylmethyloxy-1,2-napthoquinone was investigated. The results of both studies are depicted in FIG. 9. The plots depict the survival of cultured MCF7 breast cancer cells (●) and adriamycin-resistant MCF7 breast cancer cells (MCF7ADR) (○). At a concentration less than 5 μM, 4-cyclohexylmethyloxy-1,2-napthoquinone effectively and equally inhibits the growth of both MCF7 and MCF7ADR cells in culture.

Example 10

Figure 10:
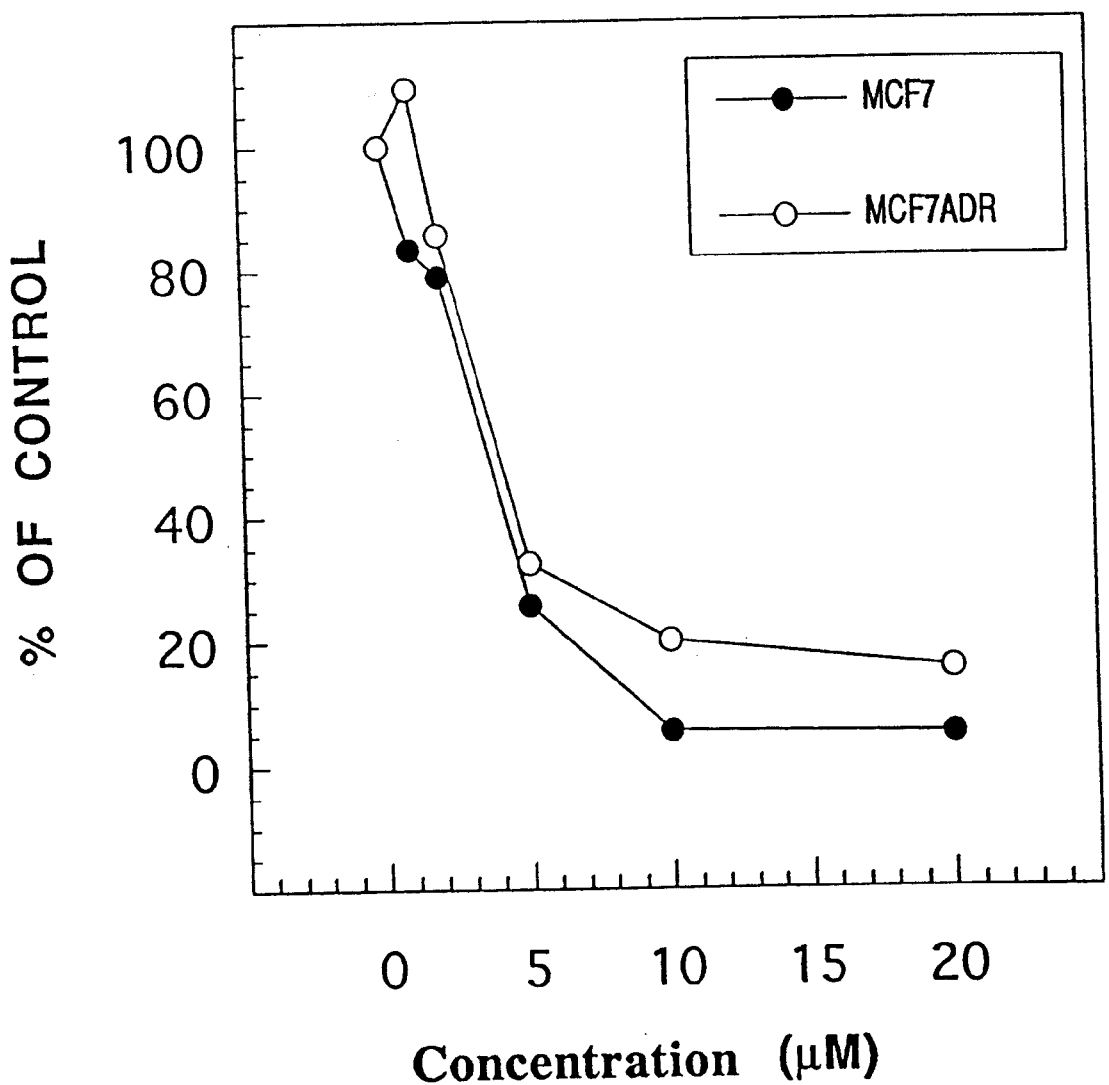
FIG. 10 is a graph showing the in vitro effect of increasing concentrations of 4-(2-pentenyloxy)-1,2-napthoquinone on the survival of cultured MCF7 breast cancer cells (●) and adriamycin-resistant MCF7 breast cancer cells (MCF7ADR) (○).

4-(2-Pentenyloxy)-1,2-napthoquinone Against MCF7 Cells and Adriamycin-Resistant MCF7 Cells Following the standard protocol, the survival of cultured human breast cancer cells MCF7 and adriamycin-resistant MCF7 cells in the presence of increasing concentrations of 4-(2-pentenyloxy)-1,2-napthoquinone was investigated. The results of both studies are depicted in FIG. 10. The plots depict the survival of cultured MCF7 breast cancer cells (●) and adriamycin-resistant MCF7 breast cancer cells (MCF7ADR) (○).

Example 11

Figure 11:
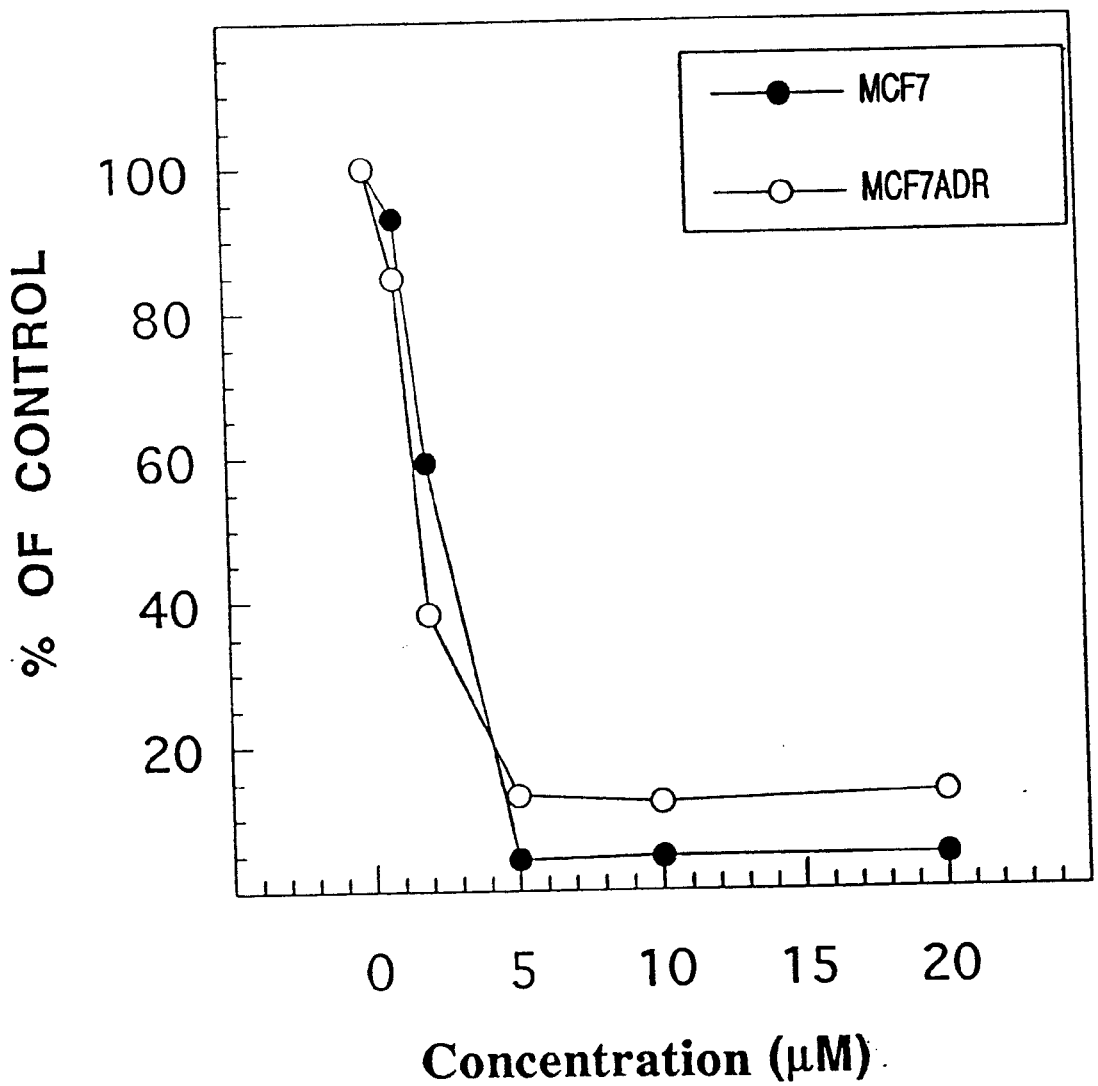
FIG. 11 is a graph showing the in vitro effect of increasing concentrations of 4-(n-heptyloxy)-1,2-napthoquinone on the survival of cultured MCF7 breast cancer cells (●) and adriamycin-resistant MCF7 breast cancer cells (MCF7ADR) (○).

4-(n-Heptyloxy)-1,2-napthoquinone Against MCF7 Cells and Adriamycin-Resistant MCF7 Cells Following the standard protocol, the survival of cultured human breast cancer cells MCF7 and adriamycin-resistant MCF7 cells in the presence of increasing concentrations of 4-(n-heptyloxy)-1,2-napthoquinone was investigated. The results of both studies are depicted in FIG. 11. The plots depict the survival of cultured MCF7 breast cancer cells (●) and adriamycin-resistant MCY7 breast cancer cells (MCF7ADR) (○). At a concentration about 5 μM, 4-(n-heptyloxy)-1,2-napthoquinone effectively inhibits the growth of both MCF7 and MCF7ADR cells in culture.

Example 12

Figure 12:
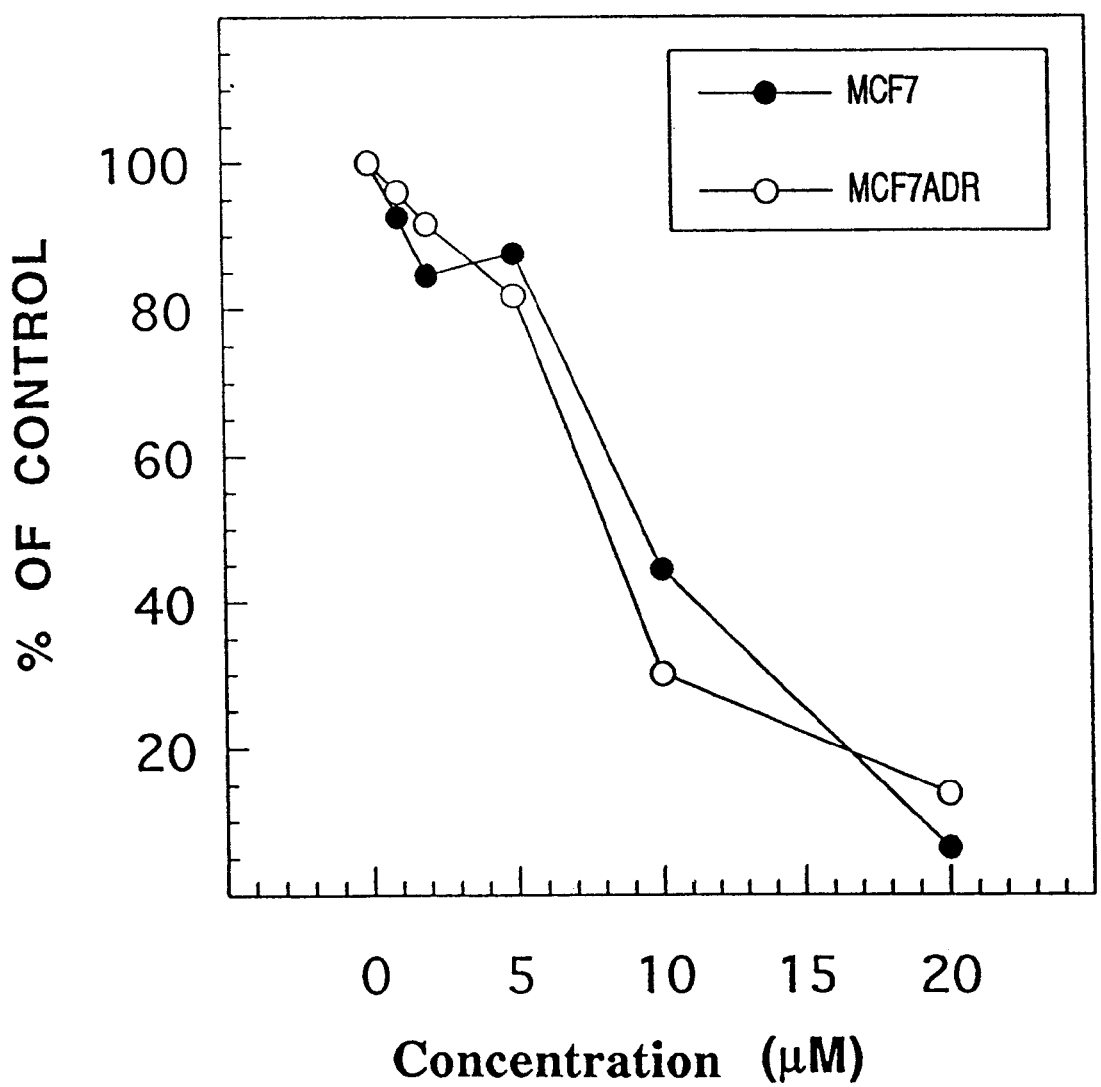
FIG. 12 is a graph showing the in vitro effect of increasing concentrations of 4-(n-pentylthio)-1,2-napthoquinone on the survival of cultured MCF7 breast cancer cells (●) and adriamycin-resistant MCF7 breast cancer cells (MCF7ADR) (○).

4-(n-Pentylthio)-1,2-napthoquinone Against MCF7 Cells and Adriamycin-Resistant MCF7 Cells Following the standard protocol, the survival of cultured human breast cancer cells MCF7 and adriamycin-resistant MCF7 cells in the presence of increasing concentrations of 4-(n-pentylthio)-1,2-napthoquinone was investigated. The results of both studies are depicted in FIG. 12. The plots depict the survival of cultured MCF7 breast cancer cells (●) and adriamycin-resistant MCF7 breast cancer cells (MCF7ADR) (○).

Example 13

Figure 13:
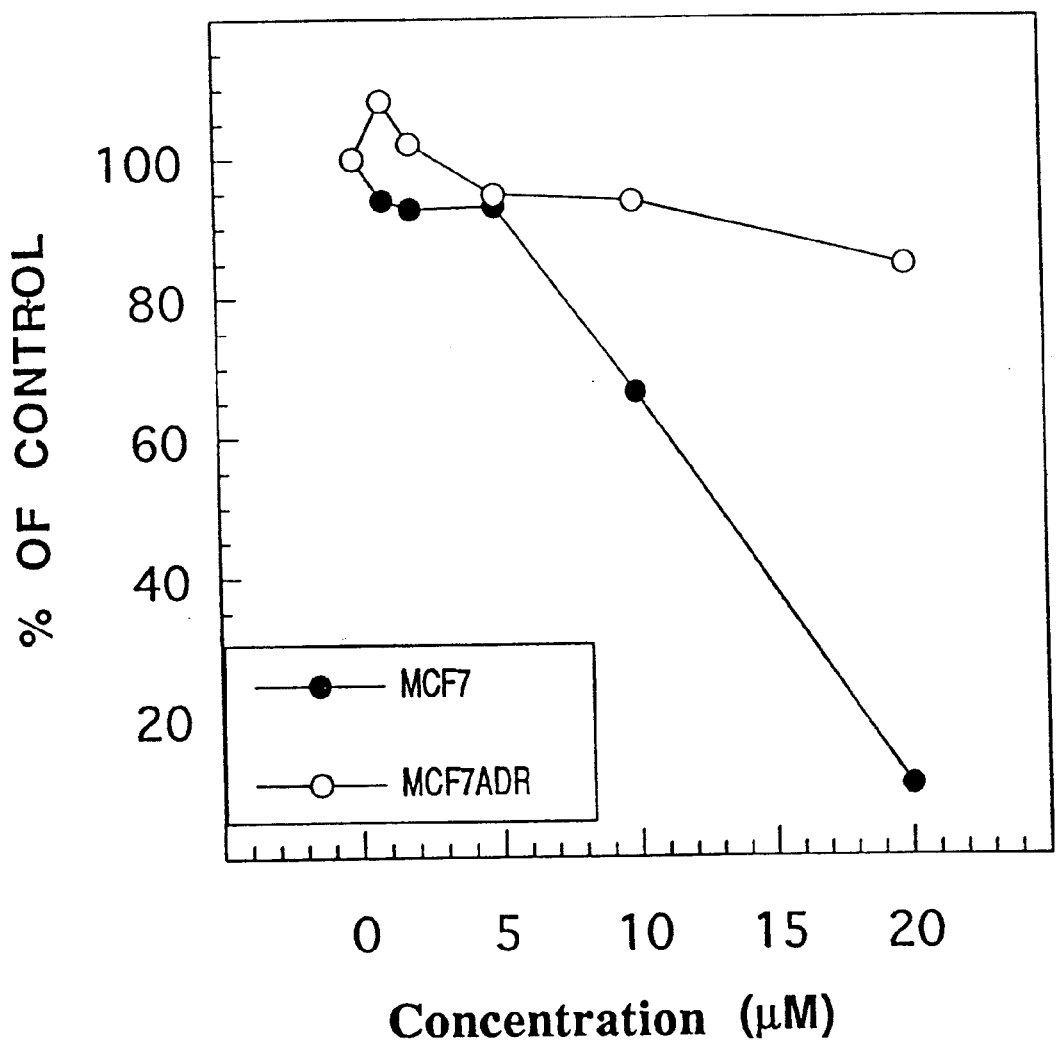
FIG. 13 is a graph showing the in vitro effect of increasing concentrations of 4-(2-N,N-dimethylamino-ethylamino)-1,2-napthoquinone on the survival of cultured MCF7 breast cancer cells (●) and adriamycin-resistant MCF7 breast cancer cells (MCF7ADR) (○).

4-(2-N,N-dimethylamino-ethylamino)-1,2-napthoquinone Against MCF7 Cells and Adriamycin-Resistant MCF7 Cells Following the standard protocol, the survival of cultured human breast cancer cells MCF7 and adriamycin-resistant MCF7 cells in the presence of increasing concentrations of 4-(2-N,N-dimethylamino-ethylamino)-1,2-napthoquinone was investigated. The results of both studies are depicted in FIG. 13. Here, the plots for the survival of cultured MCF7 breast cancer cells (●) and adriamycin-resistant MCF7 breast cancer cells (MCF7ADR) (○) are quite different. The compound tested had very little effect on the MCF7ADR cell line. But, while not as powerful as the compounds of Examples 1–12, at concentrations greater than about 10 μM, 4-(2-N,N-dimethylamino-ethylamino)-1,2-napthoquinone effectively inhibits the growth of MCF7 cells in culture.

Example 14

4-Pentyloxy-1,2-napthoquinone Against Atypical Multidrug-Resistant CEM/V-1 Cells Following the standard protocol, the survival of cultured CEM leukemia cells and the survival of atypical multi-drug-resistant leukemia cells (CEM/V-1) in the presence of increasing concentrations of 4-pentyloxy-1,2-napthoquinone was investigated. The results of these two studies indicated an $IC_{50}$ of 0.25 μM against the CEM cells and an $IC_{50}$ of 0.35 μM against the multi-drug-resistant CEM/V-1 cells.

Example 15

4-Pentyloxy-1,2-napthoquinone Against Cell Lines which Over-Express MDR1: KB3-1 and KBH-1 Cells Following the standard protocol, the survival of cultured KB3-1 and KBH-1 cell lines in the presence of increasing concentrations of 4-pentyloxy-1,2-napthoquinone was investigated. The results of these two studies indicated an $IC_{50}$ of 0.30 $\mu$M against the KB3-1 cells and an $IC_{50}$ of 0.15 $\mu$M against the KBH-1 cells.

Comparative Example

4-Ethyloxy-1,2-napthoquinone Against A549 Cells and MCF7 Cells

Figure 14:
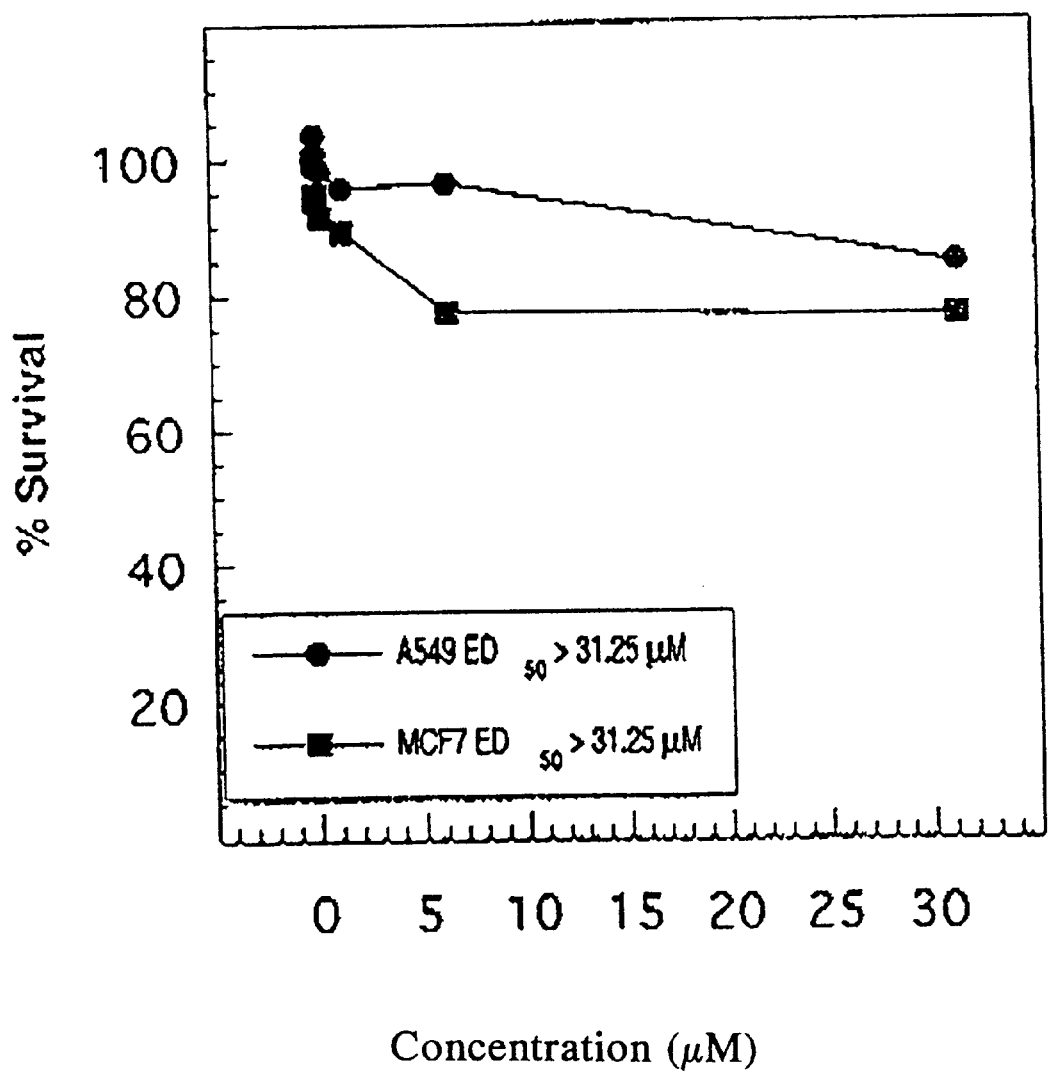
FIG. 14 is a graph of the results of the Comparative Example, showing the minimal in vitro cytotoxicity of 4-ethoxy-1,2-naphthoquinone against cultured human lung cancer cells A549 (ATCC CCL-185) (●) and cultured human breast cancer cells MCF7 (■).

Following the standard protocol, the survival of cultured human lung cancer cells A549 and human breast cancer cells MCF7 in the presence of increasing concentrations of 4-ethyloxy-1,2-napthoquinone was investigated. The results of both studies are depicted in FIG. 14. The $ED_{50}$ of the ethyloxy derivative was shown to be 31.25 $\mu$M against both the A549 cells and the MCF7 cells.

It is understood that the invention is not confined to the particular chemical reactions, reagents, solvents, transformations, or cell lines herein illustrated and described, but embraces all such modified forms thereof as come within the scope of the following claims.

What is claimed is:

1. A method of inhibiting growth of cancer cells, comprising treating the cancer cells with an effective growth-inhibiting amount of a compound of Formula I:

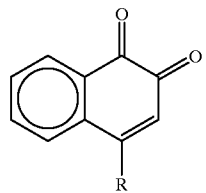

(I)

wherein R is selected from the group consisting of $C_3$–$C_8$ linear or branched alkyloxy, $C_3$–$C_8$ linear or branched alkenyloxy, $C_3$–$C_8$ linear or branched amino, $C_3$–$C_8$ alkylthio, and $C_1$–$C_8$ linear or branched substituted alkyloxy, alkenyloxy, amino, and alkylthio, substituted with one or more substituents selected from the group consisting of cycloalkyl, cycloalkenyl, cycloaryl, benzyl, and amino; pharmaceutically-suitable salts thereof, and combinations thereof.

2. The method of claim 1, wherein an amount of one or more compounds of Formula I is administered to a human cancer patient in need thereof which is effective to inhibit the growth of the cancer cell.

3. The method of claim 2, wherein the amount of one or more compounds of Formula I is administered parenterally in combination with a pharmaceutically-acceptable liquid or solid carrier.

4. The method of claim 2, wherein the amount of one or more compounds of Formula I is administered intravenously in combination with a pharmaceutically-acceptable liquid carrier.

5. The method of claim 2, wherein the amount of one or more compounds of Formula I is administered orally in combination with a pharmaceutically-acceptable liquid or solid carrier.

6. The method of claim 2, wherein one or more compounds selected from the group consisting of 4-pentyloxy-1,2-napthoquinone; 4-(2-methyl-propyloxy)-1,2-napthoquinone; 4-(3-methyl-butyloxy)-1,2-napthoquinone; 4-(isopropyloxy)-1,2-napthoquinone; 4-(2-butenyloxy)-1,2-napthoquinone; 4-benzyloxy-1,2-napthoquinone-;4-cyclohexylmethyloxy-1,2-napthoquinone; 4-(2-pentenyloxy)-1,2-napthoquinone; 4-(n-heptyloxy)-1,2-napthoquinone; 4-(n-pentylthio)-1,2-napthoquinone; 4-(2-N,N-dimethylamino-ethylamino)-1,2-napthoquinone, pharmaceutically-acceptable salts thereof, and combinations thereof, is administered to the patient.

7. The method of claim 2, wherein an effective growth-inhibiting amount of a compound of Formula I is administered to a human cancer patient suffering from a multiple-drug resistant cancer.

8. The method of claim 7, wherein an effective growth-inhibiting amount of a compound of Formula I is administered to a human cancer patient suffering from an adriamycin-resistant cancer.

9. The method of claim 7, wherein an effective growth-inhibiting amount of a compound of Formula I is administered to a human cancer patient suffering from a teniposide-resistant cancer.

10. The method of claim 7, wherein an effective growth-inhibiting amount of a compound of Formula I is administered to a human cancer patient suffering from a vinblastine-resistant cancer.

* * * * *